United States Patent [19]

Reid

[11] 4,174,385

[45] Nov. 13, 1979

[54] METHOD OF IDENTIFICATION OF SURFACE PROTEINS OF CANCER CELLS, CLINICAL TEST AND METHOD OF IMMUNIZATION

[75] Inventor: Robert H. Reid, 910 Rivenoak, Birmingham, Mich. 48008

[73] Assignees: Robert Reid; Robert Alpern; Allan B. Schmier; Sheldon A. Fealk; Jerry Michael Ellis, all of Southfield, Mich. ; a part interest to each

[21] Appl. No.: 730,764

[22] Filed: Oct. 8, 1976

[51] Int. Cl.$^2$ ...................... A61K 43/00; G01N 33/16
[52] U.S. Cl. ................................ 424/1; 260/112.5 R; 424/12
[58] Field of Search .................. 260/112.5; 424/1, 1.5, 424/12

[56] References Cited

U.S. PATENT DOCUMENTS 4,041,023   8/1977   Felix et al. .................... 260/112.5 R Primary Examiner—Benjamin R. Padgett
Assistant Examiner—Christine M. Nucker
Attorney, Agent, or Firm—Cullen, Sloman, Cantor, Grauer, Scott & Rutherford

[57] ABSTRACT

It has now been determined that cancer cells have a specific surface protein existing as a glycoprotein which functions to stimulate specific cell-mediated immune response in the host directed toward the specific cancer. The following disclosure includes the method of identification of the specific cell surface protein and procedures utilizing the protein, or preferably the active peptide in testing for specific cancers and immunization. Having identified the specific cell surface protein for a cancer, the n-terminal tridecapeptide or the active portion of the peptide may be synthesized and utilized in testing and immunization. Further, the specific cell surface protein and active peptide for ductal carcinoma (brest cancer) is identified herein.

7 Claims, No Drawings

METHOD OF IDENTIFICATION OF SURFACE PROTEINS OF CANCER CELLS, CLINICAL TEST AND METHOD OF IMMUNIZATION

FIELD OF THE INVENTION

Generally, the present invention relates to a method of identification of cancer cell surface proteins for specific cellmediated immunity, permitting synthesis of the active peptide and use of the synthetic peptide in diagnostic procedures and immunization.

A viral etiology for ductal carcinoma (breast cancer) has long been suspected. Prior researchers have found evidence of a common tumor surface antigen (TSA) resulting in cross immunity in animal viral induced tumors, Hellstrom et al, Ann. rev. microbiol. 24,373 (1970), Kline, Israel J.Med. Sci. 7, 111, (1971), etc. in contrast to carcinogen induced tumors, Prehn et al J. Nat. Cancer Inst. 18, 769 (1957). The cell lines used in these studies are not producing viruses, Cailleau et al, J. Nat. Cancer Inst. 53, 661 (1974). However, they do have multiple chromozomal markers, Seman et al, Cancer 37, 1814 (1976), Nelson-Rees, et al, Science (1976). Therefore, it appears likely that there is a non-replicating common DNA virus present in the cellular genome which is responsible for the malignant transformation and which has a cell surface product—the identified tumor surface active protein. An alternate explanation could be a non-replicating RNA virus acting via DNA transferase, Chopra et al, Cancer Res. 30, 2081 (1970). This would account for RNA B type virus particles seen in some breast cancer cells and human milk, Rauscher et al, *Cancer Medicine*, p. 15 (1973).

Prior researchers have failed to identify a common denominator for all cancer cells although h glycoproteins have been identified in certain cancer cells. The presence of a common TSA protein in ductal carcinoma has now been discovered by the method of this invention. This method may now be utilized to identify TSA protein in other cancers. Once identified, the protein may be synthesized and utilized in diagnostic tests for cancer and immunization.

SUMMARY OF THE INVENTION

An identical protein was found by the method of this invention on the cell surface of the established ductal carcinoma cell lines. The protein was found to have the following amino acid sequence through the first 27 residues:

| 1 | | | | 5 |
|---|---|---|---|---|
| glysine | - asparagine | - threonine | - isoleucine | - valine |
| | | | | 10 |
| alanine | - valine | - glutamic acid | - leucine | - aspartic acid |
| | | 13 | | 15 |
| threonine | - tyrosine | - proline | - glutamic acid or glutamine | - threonine |
| | | | | 20 |
| aspartic acid or asparagine | - isoleucine | - glysine | - glutamic acid or glutamine | - proline |
| | | | | 25 |
| aspartic acid or asparagine | - leucine | - isoleucine | - leucine | - glutamic acid or glutamine |
| 27 | | | | |
| glysine | - aspartic acid or asparagine | | | |

Further, it has been found that the n-terminal tridecapeptide includes most, if not all, of the active sites of the protein. Therefore, the tridecapeptide may be synthesized and utilized in diagnostic tests for ductal carcinoma or immunization. Further, it is known that the carbohydrate moiety of the glycoprotein is attached to the protein at either the asparagine at position 2 or the aspartic acid residue at position 10, indicating that an octapeptide may be synthesized including the active site of the tridecapeptide.

Generally, the method of identification of the neoplastic cell surface antigen protein for specific cell-mediated immunity is as follows. First, the neoplastic cells are separated for analysis and suspended in an aqueous solution which maintains the biological activity of the protein. In the preferred method, the neoplastic cells are washed in KCl with potassium phosphate buffer. The solution is then permitted to settle and the solution including the glycoprotein is removed from the agglutinated cells. The supernatent is then dialized with phosphate buffered solution, maintaining the biological activity of the glycoproteins removed from the neoplastic cells.

The glycoproteins having more than 60% carbohydrate moiety are then separated from the solution by a hot phenol extraction method. This method includes treating the solution with heated phenol, cooling the solution and permitting the phenol and aqueous solution to separate. It has been discovered that the specific surface antigen protein is more soluble in water than in phenol and therefore the surface antigen will separate into the aqueous phase. The phenol is then removed from the sample. The sample is then lyophilized and the precipitate is treated with chilled alcohol. The precipitate is then removed for further processing. The precipitate now includes only one Concavalin A receptor, the specific TSA protein The TSA protein is then removed by the Concavalin A method, which includes washing the solution including the TSA protein over a surface containing Concavalin A. This binds the protein to the Concavalin A. The TSA protein may then be displaced with a sugar solution. The TSA protein is removed from the sugar solution. Finally, the amino acid sequencing of the TSA protein may be determined by standard protein chemistry.

Once the neoplastic cell surface antigen protein for specific cell-mediated immunity has been identified, the active peptide may be synthesized and utilized for diagnostic procedures or immunization. As stated above, it has now been discovered that the tridecapeptide includes the active sites of the TSA protein. Further, it is believed that in most, if not all, cancers, the active sites of the protein are found in eight amino acids. The method of immunization of this invention would then include synthesizing at least eight amino acids in sequence from the n-terminal tridecapeptide of the neoplastic cell surface antigen protein for specific cell-mediated immunity, which may be identified by the method set forth above. The peptide is then conjugated with an adjuvant which is non-toxic to the subject to be immunized. Finally, the conjugate is injected into the host to raise specific immunity to the peptide, resulting in the immunity of the host to the specific cancer. The peptide may also be utilized to identify cancer in a subject by developing an antisera in a heterologist animal, conjugating the antisera with a detectable tag and treating the cells or serum to be tested for cancer with the conjugate by standard techniques. For example, where the tag is a radioactive element, standard radioimmunoassay techniques may be utilized. Finally, the active peptide may be utilized in a conventional skin test to determine the immunity of a subject to a specific cancer. The skin test would then include injecting the specific peptide or its conjugate under the skin or intradermally. The injection is then examined for a delayed reaction. If a reaction occurs, the patient has an immunity to the specific cancer and, depending upon the degree of reaction, the immunity may be increased or boosted by the method of immunization defined above.

Other advantages and meritorious features of the present invention will be more fully understood from the following detailed description.

DETAILED DESCRIPTION OF THE INVENTION

The method of isolation and identification of TSA proteins for specific cell-mediated immunity will be described herein in regard to ductal carcinoma (breast cancer). However, it will be understood that substantially the same method, or the identical method, may be utilized to isolate and identify the neoplastic cell surface antigen protein for specific cell-mediated immunity for each cancer. It is presently believed that each cancer has a unique TSA protein for specific cell-mediated immunity. As described below, once the TSA protein is identified, the active peptide may be synthesized and utilized in diagnostic tests for the specific cancer and for immunization.

It will be understood that the method of the present invention maintains the biological activity of the glycoprotein, which is important for the further procedures set forth hereinbelow. In the particular test for ductal carcinoma, breast cancer cells grown in tissue monolayers were removed with versene, washed and suspended at approximately $10^8$ cells per 30 mls. media. The cells were then pelleted by centrigation. The cells are then washed twice with saline, repelleted, saline removed, and 8 mls. of cold, 3 molar KCl with 0.005 molar potassium phosphate buffer added to the cells. The cells are then washed with approximately 2 mls. of 3 molar KCl with potassium phosphate buffer in a 125 ml. erlemyr flask. The flasks are then placed on a rocker shaker at 4° centigrade for approximately 16 hours. Then, the solution is removed by aspiration, leaving the agglutinated cells. The aspirated solution is centrifuged at 40,000 g for 60 minutes at 4° centigrade. The supernatant is then set up in dialysis against 200 volumes of deionized water at 4° centigrade for 60 minutes, times 2. The sample is then dialyzed for 48 hours with two changes of potassium phosphate buffered saline (saline at 0.15 molar and potassium phosphate at 0.01 molar) at 4° centigrade. It has been discovered that this method will maintain the glycoprotein in solution while maintaining their biological activity for up to six months at 4° centigrade.

The TSA protein eluated from the surface of the neoplastic cells by the previously described hyperosmolar potassium chloride procedure is then further treated with hot phenolic extraction. It has been discovered that the specific surface antigen or TSA protein is more soluble in water than in phenol. This method thus separates the specific surface antigen together with other glycoproteins having more than 60% carbohydrate moiety. The general method of hot phenol extraction has been utilized by others for extraction of RNA, see *Girard, Methods in Enzymology*, Vol. XII, p. 581 (1973). The method described in the publication is limited to isolation of RNA and therefore does not suggest isolation of TSA glycoproteins as determined herein.

In the present method, 21 mls. of sample was added to 20 mls. of 88% phenol at 60° centigrade. The sample was then shaken vigorously by hand in a water bath having a temperature of 60° centigrade for 30 minutes. The solution is then transferred to centrifuge tubes, precooled in ice and allowed to stand for 10 minutes. The centrifuge tubes are then centrifuged for 5 minutes at 1,000 g at 0° to separate the phases. The aqueous phase will separate to the top and the phenolic phase settles to the bottom. The aqueous phase and the whitish interphase is then separated by aspiration and the phenolic phase is discarded. The phenolic extraction is repeated with the aqueous phase and the interphase with 13 mls. of 88% hot phenolic at 60° centigrade. Again, the specimen is shaken vigorously by hand in a 60° centigrade water bath for 2 minutes and the specimen is transferred immediately to test tubes precooled in ice and allowed to stand for 10 minutes. The centrifuge tubes with the specimen are centrifuged again for 5 minutes at 1,000 g at 0° centigrade to separate the phases. Again, the aqueous phase and the whitish interphase are separated by aspiration and the phenolic phase is discarded. The phenolic extraction method described above is repeated again with the aqueous phase and the interphase with 10 mls. of 88% phenolic at 60° centigrade, shaken in the water bath described, permitted to stand and centrifuged.

The aqueous phase with the interphase is then lyophilized. The lyophilized specimen is then suspended with 20 mls. of 95% alcohol which has been chilled on dry ice and aliquoted into four centrifuged tubes which have been precooled in ice with 5 mls. each. The specimens are then centrifuged at 1,000 g at 0° centigrade for 5 minutes and the alcohol is removed by aspiration and the entire process repeated for a total of three times. The white precipitate is then brought up along with the centrifuge tube in a thin layer and subsequently air dried using a vacuum apparatus. The dried specimen is then solublized in CMM buffer, Ph 7.6 at approximately 5 mls. per tube, but to be adjusted for the volume required for total solublization. The specimens are then transferred to dialysis bags and dialyzed against CMM buffer, Ph 7.6 for 48 hours, with two changes at approximately 200 times the volume at 4° centigrade. The specimens are then lyophilized and the lyophilized specimen is solubilized in 1.3 mls. of CMM buffer, Ph 7.6. Approximately 0.3 mls. is then removed for protein determination and the remaining 1 ml. is then dialyzed against CMM buffer, Ph. 7.6 at 200 times volume at 4° centigrade for 48 hours, with two changes.

The specimen now includes only one Concanavalin A receptor, which may be separated by the Concanavalin A receptor method. The general method of isolation of a Concavalin A receptor is described in *Biochemistry*, Vol. 14, No. 1, p. 109 (1975). This method has not, however, been utilized to isolate the specific TSA protein. It has now been discovered that the combination of the hot phenolic extraction method described above and the Concavalin A receptor extraction will isolate the neoplastic cell surface antigen protein. Generally, the Concanavalin A method includes washing the solution of glycoproteins over surfrose beads having Concanavalin A. The specific surface antigen binds to Concanavalin A and the remainder of the solution is washed from the beads. Then, the surface antigen is displaced from the Concanavalin A with a sugar, such as alpha-methylglucoside.

More specifically, in the present test, 1 ml. of specimen in CMM buffer is applied to a Concanavalin A suforse column, 10 centimeters high and 9 millimeters in diameter. The column is washed with 15 mls. of CMM buffer. The effluent is monitored with 280 mu. The glycoprotein is then eluated with the alpha-methylglucoside or methyl alpha-d-glucopyranoside in CMM buffer using approximately 50–100 cc's. The specimen is then dialyzed for 6 days against CCM buffer at 40 times volume at 4° centigrade, with one change. The specimen is then dialyzed against distilled water at 4° centigrade for approximately 8 hours. The specimen is finally lyophilized in approximately 100 mls. volume.

Using the above procedure, an identical protein was found on the cell surface of different established ductal carcinoma cell lines. The protein was eluted by the hyperosmolar 3 M KCl treatment, subsequently isolated and found to have the following amino acid sequence through the first 27 residues:

| 1 glysine | - asparagine | - threonine | - isoleucine | 5 - valine |
|---|---|---|---|---|
| alanine | - valine | - glutamic acid | - leucine | 10 - aspartic acid |
| threonine | - tyrosine | 13 - proline | - glutamic acid or glutamine | 15 - threonine |
| aspartic acid or asparagine | - isoleucine | - glysine | - glutamic acid or glutamine | 20 - proline |
| aspartic acid or asparagine | - leucine | - isoleucine | - leucine | 25 - glutamic acid or glutamine |
| 27 glysine | - aspartic acid or asparagine | | | |

The ductal carcinoma cell surface antigen protein or TSA protein was tested with circulating lymphocytes using the indirect macrophage migration inhibition assay, see Thor et al, Nature 219, 5155 (1968), Rocklin et al, *In Vitro Methods In Cell-Mediated Immunity*, Bloom & Glade, Ed. (Academic Press, New York, 1971) and Adams et al, J. Nat. Cancer Inst. 56, 1119 (1976). The macrophage migration inhibition test has been demonstrated to be a reliable in vitro method for testing cell-mediated immunity, George et al, Proc. Exp. Biol. Med. 111, 514 (1962). Highly significant positive responses were found in patients with ductal carcinoma against the TSA protein from the cancer cell lines. The TSA protein from cell lines which did not have ductal carcinoma did not produce migration inhibition in control experiments. Further, normal female patients, patients with fibrocystic disease (breast), squamous cell carcinoma (lung), colo-rectal adeno carcinoma did not demonstrate positive responses when their lymphocytes were assayed using multiple doses of TSA from the ductal carcinoma cell lines. Therefore, it can be said that the ductal carcinoma cell surface antigen for specific cell-mediated immunity is unique to ductal carcinoma.

Having determined the amino acid sequence of the first 27 residues, the n-terminal tridecapeptide was synthesized to determine whether the tridecapeptide included the active site or sites. The method of synthesis may be found in *The Proteins* by Finn & Hoffmann, 3rd Ed., Vol. 2, edited by Neurath & Hill (1976). The synthetic n-terminal tridecapeptide was tested with circulating lymphocytes using the indirect macrophage migration inhibition assay. In this test, the synthetic peptide triggered MIF production from the lymphocyte of patients with ductal carcinoma. Comparing the results of these tests with the tests using the TSA protein, the potency of the tridecapeptide was found to be about 50 fold, which would indicate that probably only one antigen site exists, residing within the n-terminal tridecapeptide of the TSA protein.

Further, the prior publications of Salvinand et al, Int. Arch. Allergy 31, 366 (1967) and Spitler et al, J. Exp. Med. 136, 156 (1972) suggest that the actual antigen active site of the n-terminal tridecapeptide is eight amino acids in length. Further, as described above, it is believed that the carbohydrate moiety of the glycoprotein is attached to the tridecapeptide at either the asparagine (position 2) or the aspartic acid residue (position 10). Thus, an octapeptide may be synthesized which will include the active site. For example, if the carbohydrate moiety is attached to the glycoprotein at the asparagine, the sequence may be three to ten, four to eleven, five to twelve or six to thirteen. Alternatively, if the carbohydrate moiety is attached to the aspartic acid residue, the octapeptide may be one to eight or two to nine. Thus, it is believed that the peptide should include at least eight amino acids in sequence from the tridecapeptide.

Having isolated and identified the active peptide, the peptide may be synthesized or used directly in clinical tests for the specific cancer and for immunization against that cancer.

The clinical or diagnostic procedures for testing for the presence of a glycoprotein are well known. For example, human chorionic gonadotropin has been detected very early in human gestation and is now used as a diagnostic test for pregnancy. The concentration of hCG in both maternal blood and urine rises to a maximum during the first trimester of pregnancy and declines thereafter to a low level during the latter portion of pregnancy. The presence of hCG, which is a glycoprotein, is determined by standard radioimmunoassay techniques. Briefly, the procedure is as follows. The antiserum specific to the peptide or glycoprotein is raised by serially injecting the glycoprotein or peptide into a heterologist animal, commonly rabbits. The animal is then bled and the antiserum is extracted and purified as described in Naughton et al, Cancer Research, Vol. 35, p. 1887 (1975). Where a radioactive isotope is utilized as the label, such as radioiodine 125, radioiodine 131 or tritium, the antisera is conjugated to the radioactive isotope.

Where a double-antibody technique is utilized, the second antiserum must be specific to the first antiserum. For example, where the first host animal is a rabbit, anti-rabbit gamma globulin is used. For example, rabbit immunogamma globulin G (IgG) is injected into a second host animal, such as a sheep or goat. The second host animal is then bled and the anti-rabbit gamma globulin is extracted, purified and labeled by conjugation to the preferred label. Methods of conjugating fluorescein and radioiodine to an anti-rabbit gamma globulin are described in *Methods In Enzymology*, Watkins, Academic Press (1975). Alternatively, the tridecapepitide or the active octapeptide may be conjugated directly to the detectable label by a similar procedure.

The clinical procedure for determining the presence of a specific cancer would then depend upon the detectable tag (e.g. fluorescein, radioiodine, etc.) and the sample to be tested. For example, body fluids including blood, urine, etc., may be tested for the presence of the glycoprotein by radioimmunoassay techniques using a radioactive element. A cell test may use the double antibody test using a visual tag, such as fluorescein. Where fluorescein is used as a detectable tag or label, the procedure is to add appropriately diluted antiserum specific to the tridecapeptide or the active octapeptide to the sample to be tested. The sample is then incubated and rinsed, for example, with PBS. Following washing, the slides may be examined directly for the presence of fluorescein where a single antibody technique is used. Where the double antibody technique is used, the second antibody is conjugated to fluorescein as described. Following treatment with the first antiserum, the second antiserum conjugated to fluorescein is added. The slides are incubated, washed and examined, preferably with an ultraviolet microscope. If fluorescence is found, the glycoprotein is present and the presence of the specific cancer has been confirmed. A similar procedure is utilized in radioimmunoassay techniques, except that the presence of the glycoprotein is determined by measurement with a Geiger counter.

Similarly, the method of immunization or isoimmunization against a specific glycoprotein is also known. For example, Talwar et al, Vol. 13, No. 2 (15 papers) 125–258 (Feb. 1976) conjugated the beta-subunit of hCG to the adjuvant tetanus toxoid in discrete molecular proportions and injected the conjugate into women of childbearing years as an immunological method of preventing pregnancies. In the test described in the Talway et al papers, the conjugate raised the antisera to the beta-subunit of hCG and tetanus toxoid in all animals and women tested. Extensive clinical and toxicological studies by Talwar et al prove that the conjugate was safe for human use and effective to raise antibodies.

Thus, the synthetic peptide, such as the tridecapeptide or the active octapeptide may be synthesized with an adjuvant, such as a hapten including tetanus toxoid. The methods of conjugating with a hapten are set forth in Cinader et al, Br. J. Exp. Pathol. 36:515–529 (1955). The conjugate is then injected into the subject to raise the antisera to the specific peptide, stimulating specific immunity.

An individual may thus be immunized against a specific cancer by synthesizing the n-terminal tridecapeptide or active octapeptide of the neoplastic cell surface antigen protein for specific cell-mediated immunity. Then, the peptide is conjugated with an adjuvant which is nontoxic to the host. The conjugate is injected into the subject, preferably serially, to stimulate specific immunity to the peptide in the host.

Finally, it is important to clinically determine the immunity of a patient, whether or not the patient has been immunized as described above. For example, a female having ductal carcinoma will develop antibodies to the specific TSA protein. The normal method of treatment of ductal carcinoma is to excise the cancer cell mass. The patient may then have developed an immunity which will destroy the remaining cancer cells. In certain cases, however, the patient has developed an insufficient immunity or no immunity at all, requiring further treatment. Two tests have been developed for determining the presence of antibodies to the TSA protein or isoimmunization.

The skin test includes injecting the specific peptide, preferably the synthetic peptide or its conjugate under the skin or intraderminally. The injection is then examined for a delayed reaction, for example, after 24 hours. If a reaction occurs, the patient has an immunity and, depending upon the degree of reaction, the immunity may be increased or boosted by the method of immunization set forth above. Alternatively, the body fluids of the patient may be examined for the presence of antibodies by conjugating the peptide with a detectable tag, such as fluorescein or a radioactive iodine. The body fluids are then treated as described above and tested for the detectable tag. If the detectable tag is found, immunity has been confirmed. Where a radioimmunoassay has been made, the immunity of the patient may be quantitatively determined.

A method of isolation of the TSA protein or neoplastic cell surface antigen protein for cell-mediated immunity has now been disclosed. This method maintains the biological activity of the protein, permitting identification of the amino acid sequence. The active peptide of ductal carcinoma has also been identified as the n-terminal tridecapeptide having the following amino acid sequence:

| 1 | | | | 5 |
|---|---|---|---|---|
| glysine | - asparagine | - threonine | - isoleucine | - valine |
| | | | | 10 |
| alanine | - valine | - glutamic acid | - leucine | - aspartic acid |
| | | 13 | | |
| threonine | - tyrosine | - proline | | |

This method is also utilized to identify the active peptide of other cancers, permitting the synthesis of the active peptide for each specific cancer.

The active synthetic peptide may then be utilized as a clinical or diagnostic tool in detecting the presence of a specific cancer by conventional in vitro or in vivo techniques. Further, the active peptide or preferably the peptide conjugated with an adjuvant may be injected into a patient stimulating specific humoral and cell-mediated immunity to the TSA protein and therefore the specific cancer. Finally, the peptide may be utilized to determine the immunity of a patient following surgery or immunization. Having described the method of identification of surface proteins of cancer cells, the diagnostic or clinical tests and the method of immunization, it will be understood that various modifications may be made to the inventions without departing from the purview of the appended claims. Further, it will be understood that the specific TSA protein for cell-mediated immunity may now be determined for each cancer, the active peptide synthesized and used in the clinical procedures set forth above.

I now claim:

1. A method of identification of a specific cancer in a subject, comprising:
   (a) synthesizing a peptide having amino acids in sequence including the active site from the n-terminal tridecapeptide of the cancer cell surface antigen protein for specific cell immunity;

(b) developing an antisera in a heterologous animal by injecting the animal with said synthetic peptide, bleeding the animal and recovering the antisera;

(c) conjugating said antisera with a detectable tag; and (d) contacting the cells to be tested for cancer with said conjugate and determining the presence of said detectable tag.

2. A method of detecting breast cancer comprising the following steps;

(a) injecting a heterologous animal with a peptide comprising amino acids in sequence including the active site from the following n-terminal tridecapeptide:

| 1 glysine | - asparagine | - threonine | - isoleucine | 5 - valine |
|---|---|---|---|---|
| alanine | - valine | - glutamic acid | - leucine | 10 - aspartic acid |
| threonine | - tyrosine | 13 - proline | | |

(b) bleeding said animal and removing the antisera to said peptides, (c) conjugating said antisera with a detectable tag, (d) contacting the sample taken from the subject to be tested with said antisera conjugated with a detectable tag and determining the presence of said tag.

3. The method defined in claim 2, wherein said detectable tag is a radioactive element and said sample is a blood sample, including contacting said blood sample with said radioactive antisera and then determining the presence of said n-terminal tridecapeptide by detecting the presence of radioactivity in the sample.

4. A method of identification of a specific cancer in circulating body fluids, comprising the following steps:

(a) synthesizing a peptide having amino acids in sequence including the active site from the n-terminal tridecapeptide of the cancer cell surface antigen protein for specific cell immunity;

(b) conjugating said peptide with a detectable tag; and (c) contacting the body fluids to be tested with said conjugate and determining the presence of said detectable tag.

5. A method of identification of breast cancer in body fluids, comprising the steps of:

(a) synthesizing a peptide having amino acids in sequence including the active site from the following n-terminal tridecapeptide:

| 1 glysine | - asparagine | - threonine | - isoleucine | 5 - valine |
|---|---|---|---|---|
| alanine | - valine | - glutamic acid | - leucine | 10 - aspartic acid |
| threonine | - tyrosine | 13 - proline | | |

(b) conjugating said peptide with a detectable tag; and (c) contacting said body fluids with said conjugate and determining the presence of said detectable tag.

6. A method of detecting the presence of breast cancer from a blood sample taken from the subject to be tested, comprising the steps of:

(a) contacting a fraction of said blood sample with a peptide having amino acids in sequence including the active site from the following n-terminal tridecapeptide:

| 1 glysine | - asparagine | - threonine | - isoleucine | 5 - valine |
|---|---|---|---|---|
| alanine | - valine | - glutamic acid | - leucine | 10 - aspartic acid |
| threonine | - tyrosine | 13 - proline | | |

(b) detecting the presence of the antibody to said tridecapeptide in said blood fraction, the presence of said antibody indicating the presence of breast cancer in the subject.

7. The method of detecting the presence of breast cancer defined in claim 6, wherein said peptide includes at least eight amino acids in sequence selected from said n-terminal tridecapeptide.

* * * * *